(12) United States Patent
Kimmel

(10) Patent No.: US 6,793,493 B2
(45) Date of Patent: Sep. 21, 2004

(54) TOOTH RESTORATION POST

(76) Inventor: Saul S. Kimmel, 13 Dennin Dr., Menands, NY (US) 12204

( * ) Notice: Subject to any disclaimer, the term of this patent is extended or adjusted under 35 U.S.C. 154(b) by 221 days.

(21) Appl. No.: 10/139,305

(22) Filed: May 6, 2002

(65) Prior Publication Data

US 2002/0168615 A1 Nov. 14, 2002

Related U.S. Application Data

(60) Provisional application No. 60/289,888, filed on May 9, 2001.

(51) Int. Cl.⁷ .............................................. A61C 5/08
(52) U.S. Cl. ......................................................... 433/221
(58) Field of Search ................................ 433/221, 220, 433/172, 173, 175; 623/23.48

(56) References Cited

U.S. PATENT DOCUMENTS

| | | | | |
|---|---|---|---|---|
| 4,531,915 A | * | 7/1985 | Tatum, Jr. .................... | 433/173 |
| 5,348,476 A | * | 9/1994 | Cohen et al. ................ | 433/220 |
| 5,362,237 A | * | 11/1994 | Chalifoux .................... | 433/220 |
| 5,915,970 A | * | 6/1999 | Sicurelli et al. ............. | 433/220 |
| 6,299,448 B1 | * | 10/2001 | Zdrahala et al. ............ | 433/173 |

* cited by examiner

Primary Examiner—Todd E. Manahan
(74) Attorney, Agent, or Firm—Michael F. Hoffman; Hoffman, Warnick & D'Alessandro LLC

(57) ABSTRACT

A tooth restoration post having a central dowel and a plurality of filaments. During a tooth restoration procedure, the post can be inserted into a canal of the tooth. When inserted, the plurality of filaments can engage the walls of the canal to provide support for the restored tooth. A composite material can be used to further strengthen the support of the tooth.

20 Claims, 4 Drawing Sheets

TOOTH RESTORATION POST

REFERENCE TO PRIOR APPLICATION

The current application claims priority to co-pending provisional application serial No. 60/289,888, filed on May 9, 2001 and incorporated herein by reference.

BACKGROUND OF THE INVENTION

1. Technical Field

The present invention relates generally to tooth restoration, and more specifically to a tooth restoration post having a central dowel and filaments projecting therefrom.

2. Background Art

In restoring endodontically treated teeth, such as during a root canal procedure, posts are often used to support the core of the tooth, i.e., the part of the tooth that is either wholly restorative material or partially restorative material and partially tooth structure, that supports an artificial crown, direct or indirect restoration, or fixed-partial denture abutment. Presently, there are two types of posts, prefabricated and custom.

Ideally, a post should be well fitting, constructed with absolute minimal tooth structure removal, be strong, possess sufficient modulus of elasticity to absorb force and flex appropriately, reinforce and strengthen the root, utilize the canal irregularities for retention, be fabricated with minimal operator technique sensitivity, and arrest fractures and cracks within the root and prevent their extension into the periodontium. Custom posts and prefabricated posts each have some of these advantages, however they both have several disadvantages as well.

A custom post may be advantageous in that it attempts to reproduce the anatomy of the canal preparation created by the dentist to yield a post that fits the canal precisely. In other words, it is intended to be a "positive" reproduction of the canal preparation (the "negative") within the root, that can be inserted passively, and that produces no insertional or functional stresses. Additionally, it may be used where prefabricated posts are ineffective due to the size and shape of the root canal.

However, custom posts also have several disadvantages. For example, it is time consuming to implement, requiring a minimum of two visits. An initial visit is required for the construction of an impression to manufacture the post, and a subsequent visit for the insertion of the post and preparation for the restoration after the post is inserted or cemented. It is also more costly since a laboratory fee is involved. A custom post also may require the removal of additional tooth structure to create a tapered preparation that will form and unobstructed path of insertion for the laboratory fabricated custom post. This tooth structure may be desired to support an already compromised tooth which will be further compromised by the removal of additional tooth structure. The tapered preparation may create a form that acts as a "wedge" that is conducive to future root fracture due to insertional and/or functional forces.

Further, creating and inserting a custom post is skill sensitive. If all the steps are not successfully accomplished, a less than appropriate product can result. For example, the post may provide less than adequate retention for the restoration, and/or be conducive to catastrophic root damage. Other disadvantages include a lack of support or reinforcement to the root, the necessity of removing all undercuts and irregularities created during root canal therapy, a possible compromise of esthetics, an inability to extend the product past root curvatures without perforation into periodontium (i.e., it must be a straight line), and an excessive enlargement of the root canal.

Conversely, prefabricated posts consist of solid dowels fabricated from various materials and generally do not accurately fit the canal into which they are inserted because the dowel is round and very few obturated root canals are round. Hence, supportive tooth structure frequently does not surround the prefabricated post on all sides. Additionally, the diameter of the canal often needs to be widened to create a preparation to accept a post surrounded by tooth structure on all sides. The widening can obliterate the canal space, and can substantially weaken the root or lead to iatrogenic perforation of the root.

Advantageously, a prefabricated post is less expensive than a custom post. Additionally, the prefabricated post can be constructed and inserted in a single visit. Further, a crown or bridge abutment can be prepared immediately after inserting the post, and installation is generally less sensitive to the technique and/or skill of the installer.

However, the prefabricated post also has several disadvantages. The tooth is fitted to accept the post, rather than the post being fitted to the preparation of the tooth. When a parallel design is used, which allows for a more benign distribution of forces than a tapered form, tooth structure in the narrowest and thinnest portion of the root must be removed. This weakens the root, increases the susceptibility of the root to fracture during insertion and/or function, and increases the potential for an iatrogenic perforation during preparation of the post space.

Further, when there is coronal destruction that extends into the root-orifice area, a prefabricated post will not fit this area accurately. The post will be surrounded by a void that must be replaced by a restorative or cementing medium. These media are not as supportive as tubular dentin. The longer the unsupported area, the longer the fulcrum arm that is created. In other words, the ratio of unsupported post area is increased in relation to post area supported by tooth structure. This has a weakening effect on the post and produces greater stresses during function than a post that is supported by tooth structure along its entire length. Therefore, this post may fit well in one area but be poorly adapted to the root in another area.

The prefabricated post also does not provide support or reinforcement of the tooth. Other disadvantages include the possible removal of undercuts and irregularities created during root canal therapy, compromise of the esthetics, an inability to extend beyond root curvatures (i.e., the rotary cutting instrument produces a straight line), and it may excessively enlarge the canal beyond the size created during the root canal therapy.

Accordingly, a need exists for a tooth restoration post and method that provide the advantages of both the custom and prefabricated posts while overcoming the disadvantages these posts.

SUMMARY OF THE INVENTION

The present invention overcomes the above-mentioned disadvantages and provides the advantages by providing an improved tooth restoration post and method. In particular, the invention provides a post having a central dowel with filaments projecting therefrom. The filaments can engage the walls of a canal to provide support to the tooth.

A first aspect of the invention provides a tooth restoration post, comprising: a central dowel; and a plurality of filaments projecting outwardly from the central dowel.

A second aspect of the invention provides a tooth restoration system, comprising: a post having: a central dowel; and a plurality of filaments projecting outwardly from the central dowel.

A third aspect of the invention provides a method of restoring a tooth, comprising: preparing a canal of the tooth; providing a post having a central dowel and a plurality of filaments projecting outwardly from the central dowel; and inserting the post into the canal of the tooth so that the plurality of filaments engage the walls of the canal.

The exemplary aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

The invention provides a post having a central dowel and a plurality of filaments extending therefrom. The post addresses several disadvantages of custom and prefabricated posts which are limited to supporting the core without providing strength to the root.

When performing restoration of a tooth, the tooth can be initially prepared by forming an opening in the crown of the tooth. This allows the pulp present in the root canals to be removed. Next, the canals themselves are prepared for filling. This may include, for example, cleaning, enlarging, shaping, etc., the canals for filling. The canals are then filled with a filling that frequently includes a post to provide added support for the remaining tooth structure. An artificial crown, direct or indirect restoration, fixed-partial denture abutment, etc. can then be placed over the tooth to complete the tooth restoration.

A temporary filling may be placed in the canal prior to inserting a permanent filling. In the present method, removal of the temporary filling material can be performed with a heated instrument. Therefore, further enlargement of the canal beyond that done during the root canal preparation is avoided. If some apical enlargement is necessary at the apical portion, it is only minimal.

Figure 1:
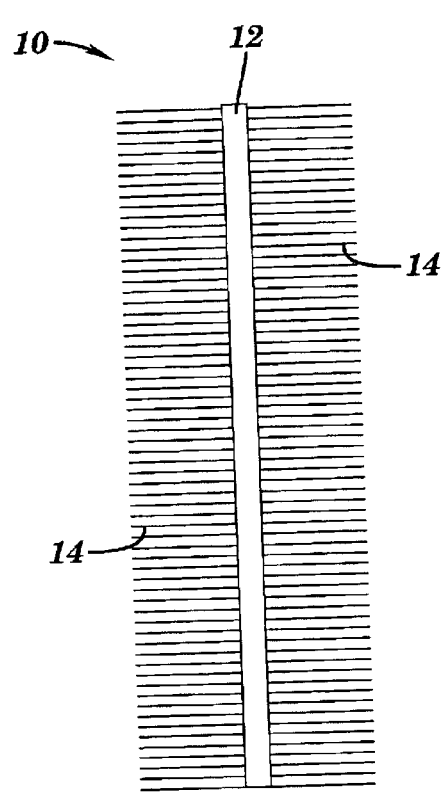
FIG. 1 is a cross-sectional side view of a tooth restoration post having substantially perpendicular filaments.

As shown in FIG. 1, the invention provides a post 10 comprising a central dowel 12 having filaments 14 projecting outwardly for use when filling a prepared canal of a tooth. As shown, filaments 14 can project out at about a 90° angle, however, any desired angle is equally applicable. Central dowel 12 can be, for example, constructed of metal or fiberglass. One aspect of the invention uses a central dowel 12 that is soft and made of a twisted metal wire or thin fiberglass. In this case, post 10 can negotiate around curves in a canal. Therefore, the length of post 10 that can be inserted into a canal is not limited by the canal having a curvature. Additionally, the possibility of perforation is minimized. Filaments 14 can be constructed of fiberglass, for example, and can also be flexible.

Figure 2:
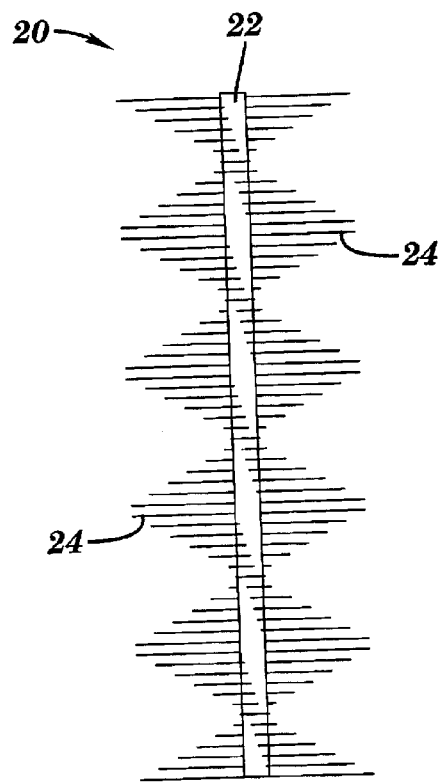
FIG. 2 is a cross-sectional side view of a tooth restoration post having filaments arranged in a spiral pattern.

The filaments may be configured to facilitate insertion of the post into a canal of a tooth. The filaments can have a spiral or auger-like pattern along a central dowel that allows the post to be twisted into place. For example, FIG. 2 is a cross-section of a side view of a post 20 comprising a central dowel 22 having a plurality of filaments 24 projecting outwardly. In this case, filaments 24 are configured in a spiral pattern to assist with the insertion of post 20 into a tooth. A removable handle (not shown) can be attached to central dowel 22 and/or filaments 24 to facilitate twisting post 20 during insertion. The handle would then be removed once post 20 is inserted into the tooth at a desired position.

Figure 3:
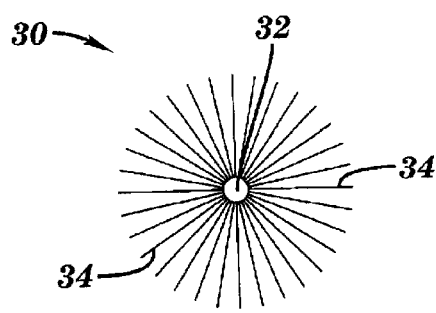
FIG. 3 is a cross-sectional top view of a tooth restoration post having filaments that form a substantially circular shape about the center of the central dowel.
Figure 5:
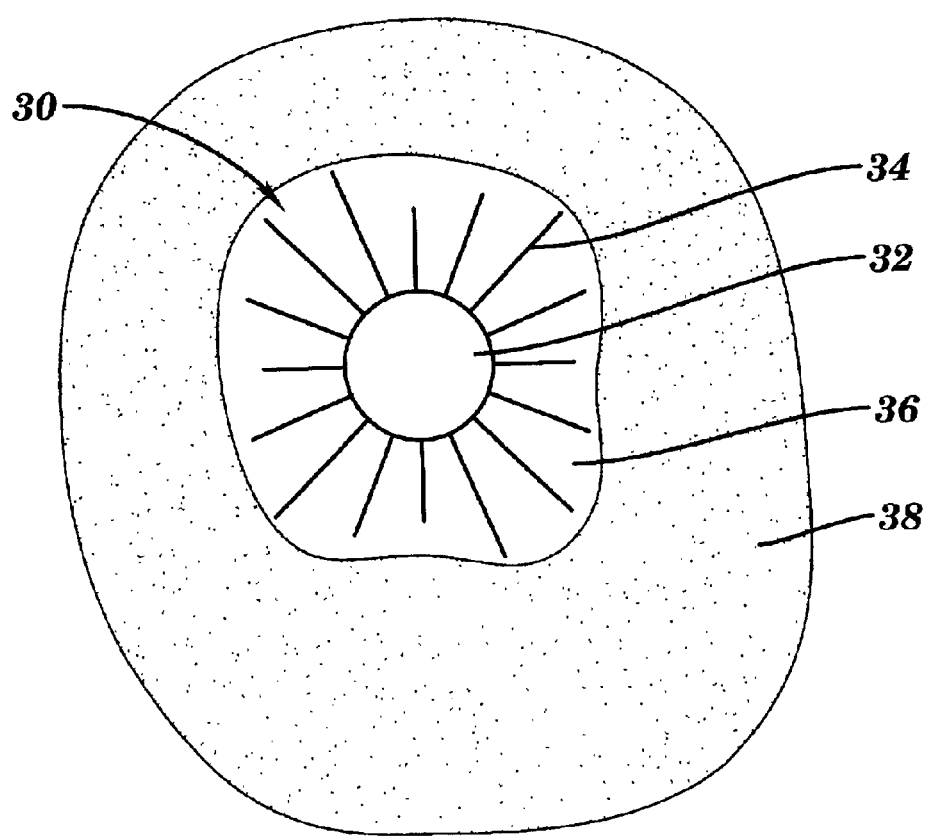
FIG. 5 is a top view of a tooth having a substantially round canal into which a post is inserted.

The filaments may extend outwardly with a radius greater than the canal so that the filaments engage the walls of the canal during insertion. FIG. 3 is a top view of a post 30 having filaments 34 projecting outwardly from a central dowel 32. As shown, filaments 34 project in all directions about central dowel 32. In this case, filaments 34 are substantially the same length and form a substantially circular shape about a center of central dowel 32. FIG. 5 is a top view of post 30 inserted into a substantially round canal 36 in tooth 38. As can be seen, post 30 conforms to and fills canal 36 to provide a very secure support.

After canal 36 has been prepared, a bonding agent can be added to canal 36. Post 30 can also be saturated with a composite material that has been conditioned for bonding. As a result, central dowel 32 and filaments 34 would be substantially coated with the composite material. This composite material can also be spun into canal 36. Post 30 can then be inserted into canal 36, and the composite material can be cured. The presence of the composite material and/or the bonding agent strengthens the support that post 30 provides to the core. Any composite material and bonding agent can be utilized, for example, a resin cement or composite restorative material. Once inserted and cured, the post-filament-composite material complex forms a solid lattice structure that substantially fills canal 36. Therefore, post 30 can provide a stable support for the core of tooth 38, and also can support an artificial crown, direct or indirect restoration, fixed-partial denture abutment, etc.

As seen in FIG. 5, when inserted, central dowel 32 is located within the central portion of tooth 38. This area receives little or no tensional or compressive stress. Therefore, the "strength" of material in this area is relatively unimportant. The strength of tooth 38 lies in its periphery.

Therefore, for post 30 to be sufficiently supportive, it should provide strength in the outer areas. For example, the support for tooth 38 and the strengthening of the root can be enhanced by filaments 34 being coated with composite material as discussed above.

Figure 6:
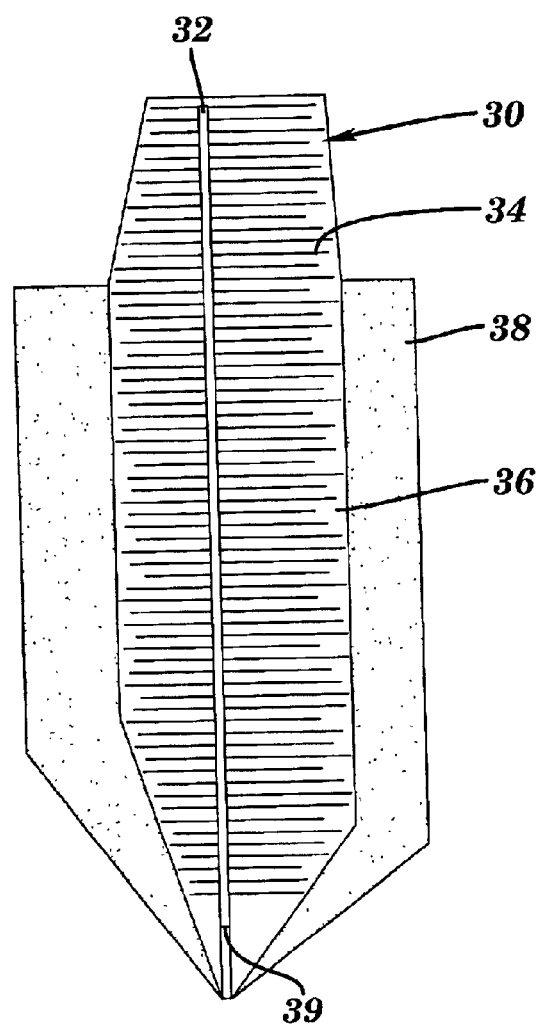
FIG. 6 is a side view of the tooth and post of FIG. 5.

It is understood that filaments 34 of varying sizes can be used, with the longest filaments 34 forming a substantially circular shape. For example, FIG. 6 is a side view of post 30 and tooth 38 as shown in FIG. 5. As can be seen, filaments 34 extend outwardly from central dowel 32 and may be of different lengths. Filaments 34 may be flexible so that the longer filaments engage and bend to meet the contours of the walls of canal 36. The shorter filaments may or may not directly engage the walls of canal 36.

In addition to supporting the core, post 30 can strengthen root 39 by forming a monoblock. This monoblock comprises a one-piece uniting of central dowel 32 and all parts of root 39 into which central dowel 32 is inserted. In other words, all parts of root 39 become fused and united with post 30 (dowel-filament-composite material) acting as the fusing medium. As a result, a supportive and strengthening effect is obtained.

Figure 4:
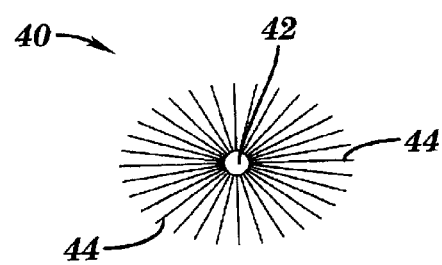
FIG. 4 is a cross-sectional top view of a tooth restoration post having filaments that form an oval shape about the center of the central dowel.
Figure 7:
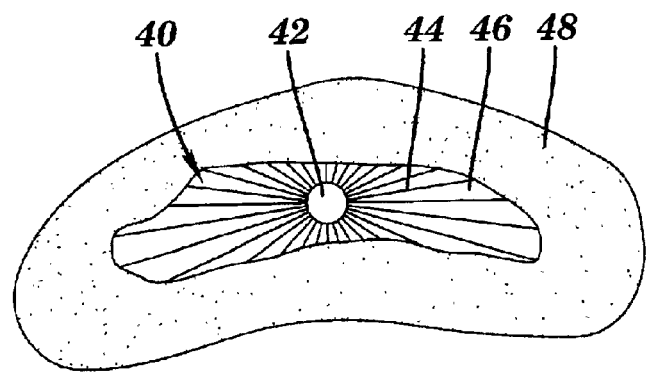
FIG. 7 is a top view of a tooth with a post inserted into an elliptical canal.

The filaments can form any shape desired. For example, FIG. 4 shows a post 40 comprising a central dowel 42 and filaments 44 projecting outwardly from and forming an oval shape about a center of central dowel 42. Post 40 may be advantageous when a canal is elliptical, sinuous, uneven, etc. FIG. 7 is a top view of post 40 inserted into an elliptical canal 46 of tooth 48. As can be seen, the longer filaments 44 engage the walls of canal 46 along the longer axis, while the shorter filaments 44 can engage the walls of canal 46 along the shorter axis of canal 46.

Figure 8:
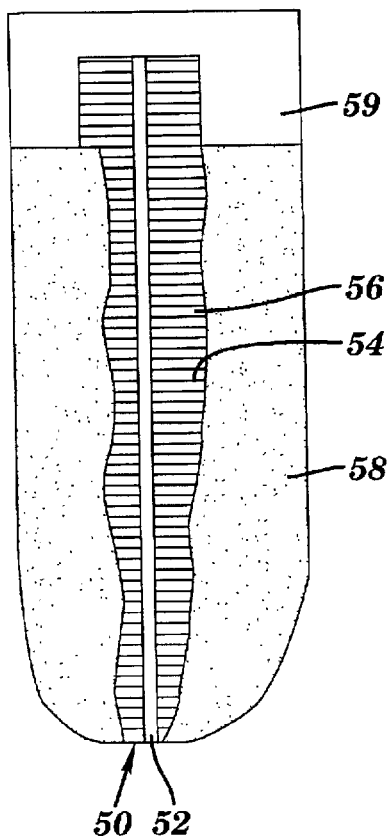
FIG. 8 is a cross-sectional side view of a tooth with an irregular canal having a post inserted.

A post of the current invention is also beneficial when the walls of a canal are irregular. As shown in FIG. 8, for example, a post 50 is inserted into a canal 56 of tooth 58. Post 50 comprises a central dowel 52 having filaments 54 projecting outwardly. As can be seen filaments 54 include sufficient length and flexibility to adapt to irregularities in canal 56 and engage the interior walls of canal 56 despite the fact that canal 56 has varying widths. Use of post 50 eliminates the requirement of enlarging canal 56 prior to inserting post 50. Therefore, tooth 58 is not further weakened by any enlargement of canal 56.

FIG. 8 shows post 50 extending above tooth 58 when inserted. In this case, the portion of post 50 that is above tooth 58 creates a flat tier that provides a vertical stop and stress bearer. When post 50 is coated with a composite material that is subsequently cured as discussed above, the vertical stop is strengthened. An artificial crown 59, direct or indirect restoration, or a fixed partial denture abutment, can then be placed over this portion of post 50 and tooth 58. This step may require that post 50 be bent so that artificial crown 59, for example, can be properly supported.

Figure 9:
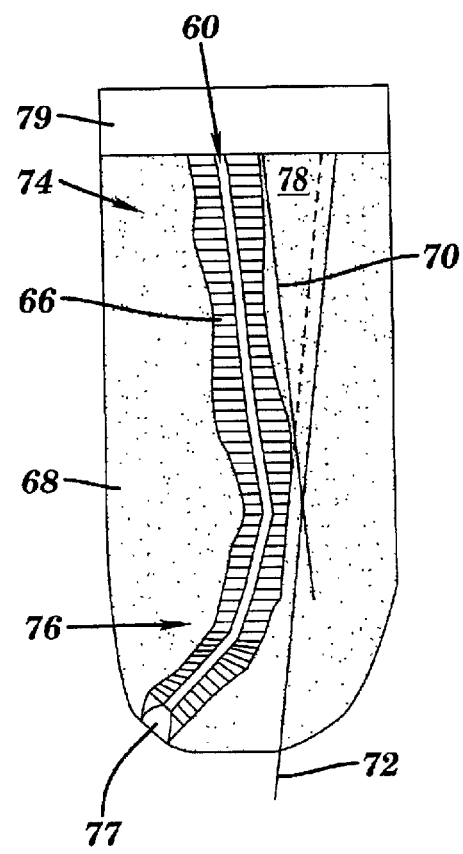
FIG. 9 is a cross-sectional side view of a tooth having a post inserted into a curved canal.

A post of the current invention can also be sufficiently flexible to negotiate around curves in a canal. For example, FIG. 9 shows a post 60 inserted into a canal 66 of tooth 68. As can be seen by the intersection of lines 70, 72, a crown portion 74 of tooth 68 frequently does not meet a root 76 in a straight line. Post 60 can fill the entire length of canal 66 without a need to remove additional tooth structure. Also shown is excess temporary filling 77, that remained after temporary filling was placed in canal 66 and subsequently removed as discussed above. Area 78 shows the additional tooth structure that would require removal to permit a straight line insertion if a rigid post was used.

FIG. 9 also shows a removable handle 79 attached to post 60. Removable handle 79 can assist in properly inserting post 60 into canal 66. For example, removable handle 79 can facilitate twisting post 60 into place. After post 60 is properly inserted into canal 66, removable handle 79 can be removed to allow the core to be constructed.

Other advantages are obtained when the filaments have a spiral pattern along the central dowel and/or when the post is twisted into the canal. For example, the filaments closely adapt to all irregularities of the canal. Additionally, incipient fractures in the tooth may be sealed, thereby arresting any continued propagation; the canal does not have to be enlarged beyond the last size endodontic instrument used, thereby preventing perforation; any canal irregularities utilized will also provide additional mechanical retention to the post; and the materials above the root (coronal) will be wider than those within the root, thus creating a perfectly adapted base or "second tier" for the post-core. This tiering provides a positive occlusal stop that promotes safety and stability.

It is understood that the figures are intended to depict only exemplary embodiments of the invention. The number of filaments, their relative size in comparison to the post, central dowel, and/or tooth, and the density shown are only schematic representations and not representative of any particular embodiment of the invention. Several variations are possible as recognized by an individual skilled in the art.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A tooth restoration post, comprising:
    a central dowel; and
    a plurality of filaments projecting radially outward from the central dowel wherein the plurality of filaments define a cross section of the post having a substantially continuous perimeter located distally from the dowel.

2. The tooth restoration post of claim 1, wherein the central dowel is flexible.

3. The tooth restoration post of claim 1, wherein the central dowel is comprised of one of the group consisting of: metal and fiberglass.

4. The tooth restoration post of claim 1, wherein the plurality of filaments are flexible.

5. The tooth restoration post of claim 1, wherein the plurality of filaments are comprised of fiberglass.

6. The tooth restoration post of claim 1, wherein the plurality of filaments are in a spiral shape to facilitate insertion.

7. The tooth restoration post of claim 1, wherein the plurality of filaments form a substantially circular shape about a center of the central dowel.

8. The tooth restoration post of claim 1, further comprising a composite material that saturates the plurality of filaments and central dowel.

9. The tooth restoration post of claim 8, wherein the composite material is hardened with a curing process.

10. A tooth restoration system, comprising:
    a post having;
        a central dowel; and
        a plurality of flexible filaments projecting radially outward from the central dowel.

11. The tooth restoration system of claim 10, further comprising a bonding agent for adding to a canal of a tooth.

12. The tooth restoration system of claim 10, further comprising a composite material that saturates the post.

13. The tooth restoration system of claim 10, further comprising a removable handle attached to the central dowel.

14. The tooth restoration system of claim 10, further comprising an artificial crown for placing over the post.

15. The tooth restoration system of claim 10, wherein the central dowel is flexible.

16. A method of restoring a tooth, comprising:

preparing a canal of the tooth;

providing a post having a central dowel and a plurality of flexible filaments projecting radially outward from the central dowel; and inserting the post into the canal of the tooth so that the plurality of filaments engage the walls of the canal.

17. The method of claim 16, further comprising adding a bonding agent to the canal of the tooth prior to the inserting step.

18. The method of claim 16, further comprising:

inserting a temporary filling into the canal after the preparing step; and removing the temporary filling prior to the inserting step.

19. The method of claim 16, further comprising:

saturating the post with a composite material prior to the inserting step; and curing the composite material, thereby forming a solid lattice structure that substantially fills the canal, after the inserting step.

20. The method of claim 16, further comprising placing an artificial crown on the tooth.

\* \* \* \* \*